US006469504B1

(12) United States Patent
Kliman et al.

(10) Patent No.: US 6,469,504 B1
(45) Date of Patent: Oct. 22, 2002

(54) METHOD AND SYSTEM FOR DETECTING CORE FAULTS

(75) Inventors: Gerald Burt Kliman, Niskayuna; John Andrew Mallick, Scotia; Manoj Ramprasad Shah, Latham, all of NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/575,715

(22) Filed: Jul. 28, 2000

(51) Int. Cl.[7] ............................................... G01N 27/72
(52) U.S. Cl. ...................................................... 324/228
(58) Field of Search ................................. 324/228, 233, 324/239, 240, 545

(56) References Cited

U.S. PATENT DOCUMENTS

| 4,996,486 A |   | 2/1991  | Posedel         |         |
|-------------|---|---------|-----------------|---------|
| 5,990,688 A |   | 11/1999 | Bourgeois et al.|         |
| 6,163,157 A | * | 12/2000 | Oldenkamp       | 324/545 |

FOREIGN PATENT DOCUMENTS

GB    2 044 936 A    8/1979

OTHER PUBLICATIONS

C. Rickson, et al, "Electrical Machine Core Imperfection Detection", IEEE Proceedings B (Electric Power Applications) vol. 133, No. 3, pp. 181–189.

JW Shelton, et al, "Introduction and Qualification of Digital Electromagnetic Core Imperfection Detector (EL CID) Test Equipment and Associated Robotic Delivery and Inspection Systems", Proceedings of the American Power Conference, vol. 56–II, 1994, pp. 1735–1742.

JW Shelton, et al, "A Comparative Analysis of Turbogenerator Core Inspection Techniques", Proceedings of the American Power Conference, vol. 47, pp. 643–650.

DJ Cadwell, et al, "Fast Gen III", The Proceedings of the American Power Conference, vol. 58–11, 1996, pp. 1249–1255.

J. Sutton, "Theory of Electromagnetic Testing of Laminated Stator Cores", Insight, vol. 36, No. 4, Apr. 1994, pp. 246–251.

* cited by examiner

*Primary Examiner*—N. Le
*Assistant Examiner*—Etienne P LeRoux
(74) *Attorney, Agent, or Firm*—Ann M. Agosti; Jill M. Breedlove

(57) ABSTRACT

A method for detecting core faults includes (a) positioning a magnetic yoke near at least one tooth of the core, the magnetic yoke being wound by a winding; (b) supplying current to the winding to inject magnetic flux into the at least one tooth of the core; (c) measuring a signal resulting from the injected magnetic flux; and (d) using the measured signal to detect core faults.

33 Claims, 6 Drawing Sheets

METHOD AND SYSTEM FOR DETECTING CORE FAULTS

BACKGROUND OF THE INVENTION

The invention relates generally to detecting core faults and more particularly to testing laminated cores of electric machines for interlamination short circuits.

Laminated stator cores are tested for interlamination shorts during manufacture and in operation in the course of maintenance operations. Core faults, such as faults caused by short circuited laminations, in large electric machines can be highly destructive.

As described in Posedel, U.S. Pat. No. 4,996,486, issued Feb. 26, 1991, one inspection technique includes ring excitation of the stator lamination with rated induction. This method, which indicates the effect of currents due to interlamination shorts by local temperature differences (which can be detected by an infrared scanner, for example), requires a high-power and controllable high-voltage source and excitation windings with large cross sections. The high power requirements cause this method to be impractical for field applications. Furthermore, this method includes specially winding the stator core.

As further discussed in aforementioned U.S. Pat. No. 4,996,486, another inspection technique involves measuring current fields due to interlamination shorts with weak induction. Only a low-voltage supply connection is required to magnetize the core stack at a lower magnetic flux level as compared to the rated level. This technique is commonly referred to as an ELectromagnetic Core Imperfection Detector (EL CID) test. In this method, the flux along each tooth is scanned with a special detector coil system to look for anomalies. Again, this method includes specially winding the stator core.

It would be desirable to have a method that does not require specially winding the stator core.

SUMMARY OF THE INVENTION

Briefly, in accordance with one embodiment of the present invention, a method for detecting core faults comprises (a) positioning a magnetic yoke near at least one tooth of the core, the magnetic yoke being wound by a winding; (b) supplying current to the winding to inject magnetic flux into the at least one tooth of the core; (c) measuring a signal (meaning at least one signal) resulting from the injected magnetic flux; and (d) using the measured signal to detect core faults.

In accordance with another embodiment of the present invention, a method for using a laminated magnetic yoke to measure a plurality of sections of a magnetic core comprises: (a) providing a compliant plunger for supporting yoke laminations of the laminated magnetic yoke; (b) positioning the magnetic yoke near a section of the core; (c) lowering the magnetic yoke until at least some of the yoke laminations are in contact with core laminations of the magnetic core; (d) taking a measurement; (e) lifting the magnetic yoke at least until none of the yoke laminations is in contact with any of the core laminations; and (f) repeating (b)–(e) near at least one different section of the core.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawings, where like numerals represent like components, in which:

DETAILED DESCRIPTION

Figure 1:
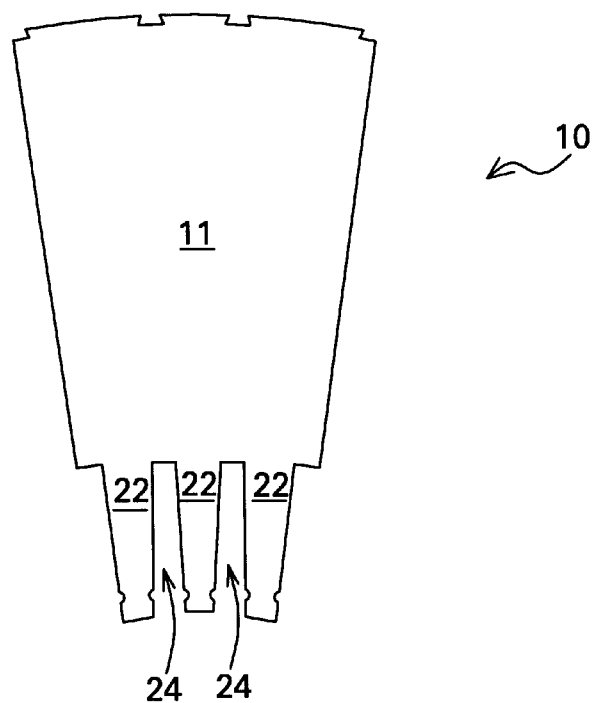
FIG. 1 is a front view of a conventional large generator lamination segment.
Figure 2:
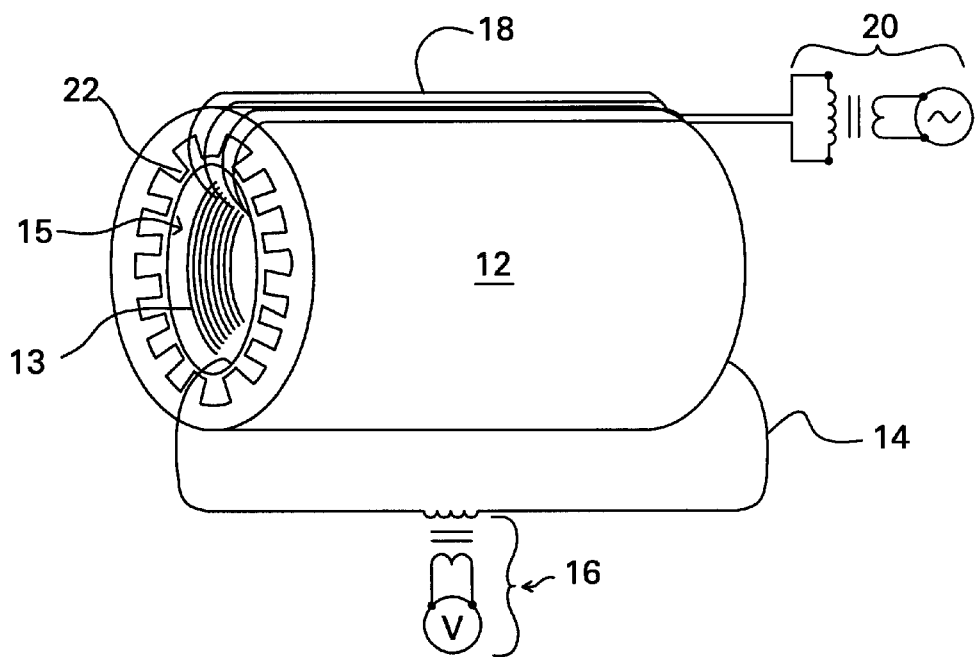
FIG. 2 is a perspective view of a conventional ring excitation system for a laminated core.

FIG. 1 is a front view of a conventional large generator lamination segment 10 including a back iron 11, teeth 22 and slots 24. Lamination segments (each about 10 mils (254 microns) to about 20 mils (508 microns) thick) are formed into a magnetic core by stacking. Typically a plurality of lamination segments (eighteen lamination segments each being twenty degrees, for one example) are used to form a complete first lamination (a lamination 13 is represented in FIG. 2, for example) with the next plurality of lamination segments forming a complete second lamination on top of and offset from the lamination segments in the first circle. The stacking continues until formation of a short stack (a stack 15 is represented in FIG. 2, for example) of about 1 inch (2.54 centimeters) to about 4 inches (10.16 centimeters) thick. A plurality of short stacks are further joined and/or clamped by bolts and/or other mechanical devices to form a stator core. A typical large generator stator core has a diameter ranging from about 8 feet (2.44 meters) to about 9 feet (2.74 meters) and a length ranging from about 30 feet (9.14 meters) to about 40 feet (12.19 meters).

FIG. 2 is a perspective view of a conventional ring excitation system for a laminated core 12 such as discussed in the background above. Although an excitation winding 18 is shown around a portion of core 12, for purposes of example, in practice, the excitation winding is often wound around the entire core. In embodiments wherein the excitation winding is not wound around the entire core, precision is reduced. In some partially-wound embodiments, the winding can be centered in the gap to reduce imprecision. Power supply 20 supplies power to the excitation winding. A search winding 14 and search winding voltage sensor 16 can be used to measure the flux level (because voltage is proportional to flux). The flux level information can be automatically or manually used to control the power supply. An infrared camera (not shown) is used to identify heat variations.

Figure 3:
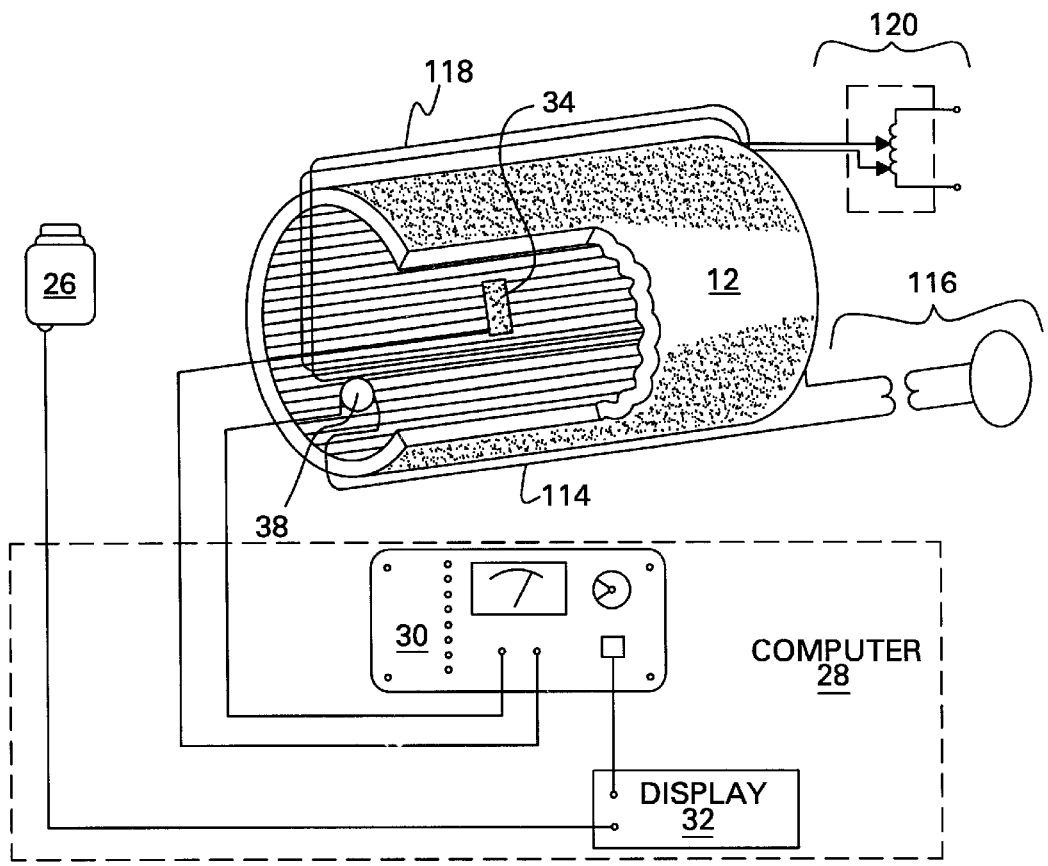
FIG. 3 is a perspective view of a conventional EL CID for a laminated core.

FIG. 3 is a perspective view of a more recent conventional EL CID for a laminated core such as discussed in the background above and further described in C. Rickson, "Electrical machine core imperfection detection," IEE Proceedings B (Electric Power Applications), vol. 133 no. 3, p.181–9, May 1986. Again excitation winding 118 is often wound around the entire core 12. Excitation winding 118 of FIG. 3 requires a much smaller diameter wire than the excitation winding of FIG. 2, and power supply 120 excites the stator core with magnetic flux at about four percent of the normal operating level. Sensor assembly 34 is scanned along each tooth by a mechanism such as a transducer 26 (which tracks the position of the sensor assembly while moving the sensor assembly) with the resulting signals being provided to a computer 28 which may comprise an analog and/or digital computer. Signal processor 30 and display or plotter 32 are shown as optional computer elements for purposes of example only.

Figure 4:
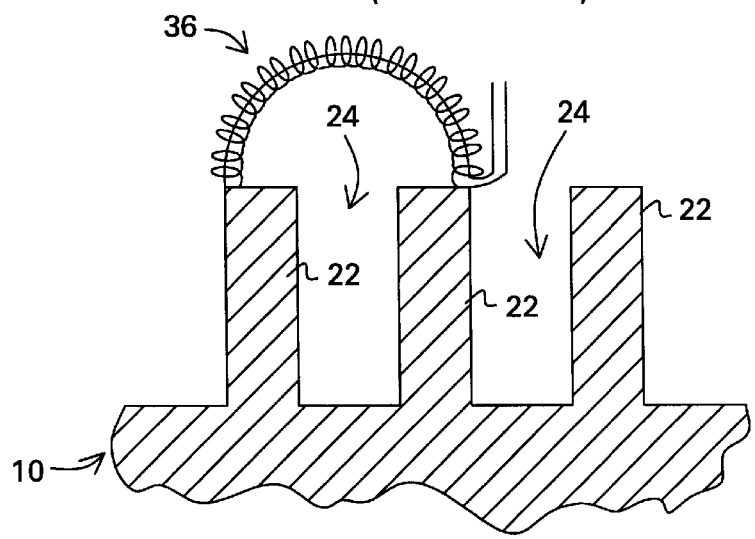
FIG. 4 is a view of a conventional Chattock magnetic potentiometer (sensing coil).

FIG. 4 is a view of a conventional Chattock magnetic potentiometer (sensing coil) for use as a sensor winding 36 in sensor assembly 34 of FIG. 3. One robotic technique for moving sensor assembly 34 (along with a sensor such as sensor winding 36) along each tooth is described in J. W. Shelton et al., "Introduction and Qualification of Digital Electromagnetic Core Imperfection Detector (EL CID) Test Equipment and Associated Robotic Delivery and Inspection Systems," Proceedings of the American Power Conference, Volume 56-II, pp. 1735–1742, 1994.

Figure 5:
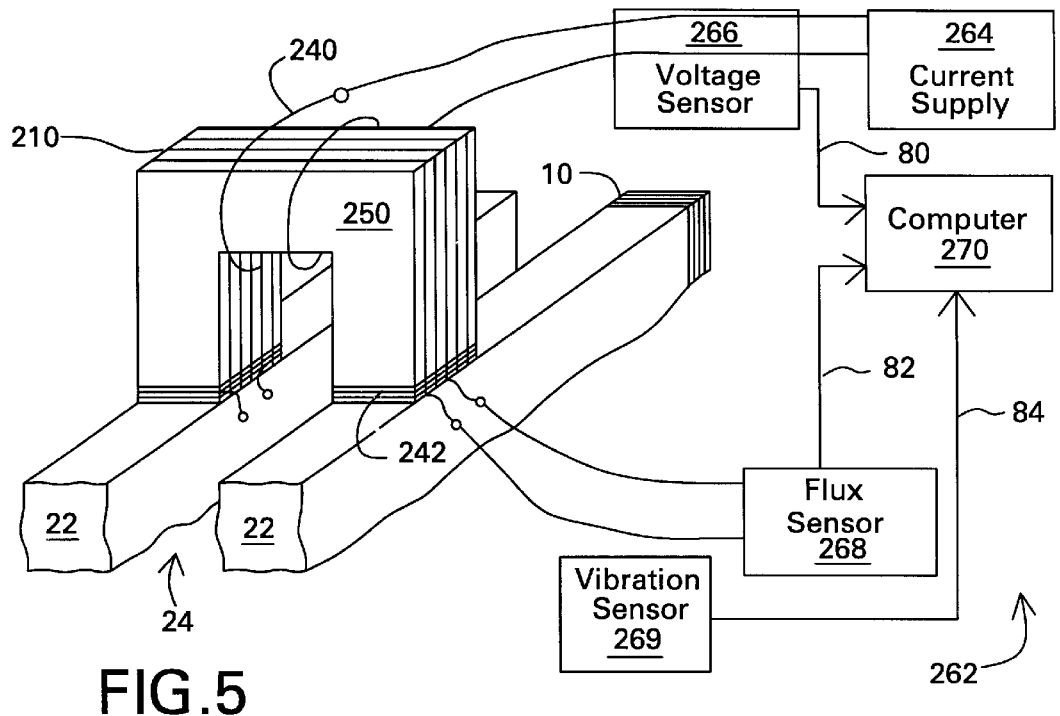
FIG. 5 is a perspective view of a system in accordance with one embodiment of the present invention.
Figure 6:
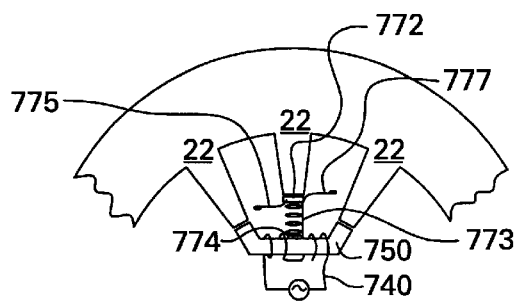
FIGS. 6–12 are views of magnetic yokes that can be used in accordance with other embodiments of the present invention.
Figure 7:
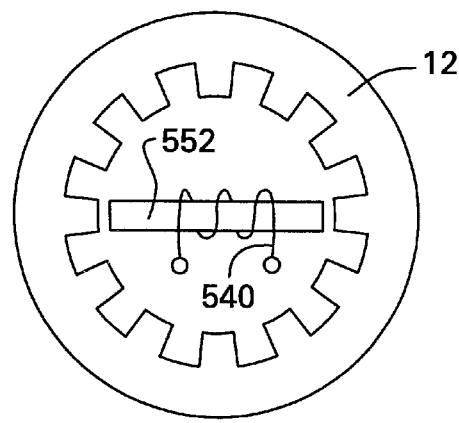
Figure 8:
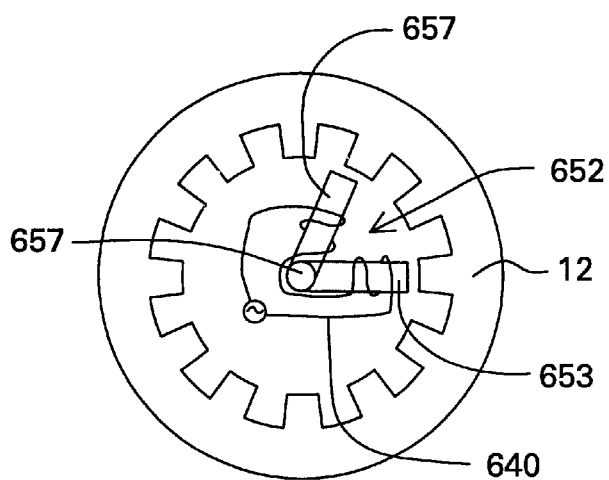

More specifically, in the embodiment of FIG. 5, the magnetic yoke is positioned near two teeth, and, even more specifically is a U-shaped (meaning U-shaped or C-shaped) yoke positioned near two adjacent teeth. Although adjacent teeth are shown in FIG. 5, the two teeth may have another tooth or multiple teeth therebetween as shown in FIGS. 6–8, for example. Referring again to FIG. 5 for purposes of example, FIG. 5 illustrates two alternative or cumulative options for a sensor (meaning at least one sensor) for measuring a resulting signal. In one example, a voltage sensor 266 is used to measure voltage across winding 240 to supply a resulting signal 80. In another example, winding 240 comprises an injection winding, the magnetic yoke is further wound with at least one flux sensing winding 242, and flux (magnitude and/or phase angle) is measured on the flux sensing winding by flux sensor 268 to supply a resulting signal 82. In a preferred variation of the flux measuring embodiment of FIG. 5, flux sensing windings are present near both teeth. Resulting signals can be processed by a computer 270 which is adapted to use the signals to detect core faults.

When a small portion of the core is excited, if the laminations are well insulated from each other, the flux response to the excitation will be primarily due to the permeable core material as modified by normal hysteresis losses and eddy currents in the laminations. However, if faults exist anywhere in the excited region, circulating currents will be induced which will alter the magnitude and phase of the response. Such altered phases or magnitudes can be used as a core condition indicator when used to compare one region of the core with another region of the core or to trend a single region over time. Additionally, analysis of the signal distribution for normal conditions and known fault conditions can be used to interpret measured signals.

One advantage of the present invention over the conventional, special winding type inventions of FIGS. 2 and 3 is that short stacks of laminations (such as short stacks 15 of laminations 13 of FIG. 2) can be tested individually while stacking during core fabrication and/or during core servicing. Thus, in this embodiment of the present invention, if a fault is located, remedial measures can be taken on the affected lamination, and, if no fault is located, additional stacks can be formed and tested. In contrast, in conventional techniques, if a fault is located in the middle of a stacked core, a substantial portion of the core must be un-stacked to gain access to the fault.

FIGS. 6–12 are views of magnetic yokes that can be used in accordance with other embodiments of the present invention with similar steps and mechanisms that are discussed, for purposes of example, with respect to FIG. 5. The embodiments of FIGS. 5–8 are particularly useful for detecting faults in the back iron 11 portion of core 12, whereas the embodiments of FIGS. 9–12 are particularly useful for detecting faults in teeth 22 of core 12. Any of the embodiments of FIGS. 5–12 can be used singly or in combination with one or more others of the embodiments.

More specifically, in the embodiment of FIG. 5, the magnetic yoke is positioned near two teeth, and, even more specifically is a U-shaped (meaning U-shaped or C-shaped) yoke positioned near two adjacent teeth. Although adjacent teeth are shown in FIG. 5, the two teeth may have another tooth or multiple teeth therebetween as shown in FIGS. 6–8, for example. Referring again to FIG. 5 for purposes of example, FIG. 5 illustrates two alternative or cumulative options for a sensor (meaning at least one sensor) for measuring a resulting signal. In one example, a voltage sensor 266 is used to measure voltage across winding 240. In another example, winding 240 comprises an injection winding, the magnetic yoke is further wound with at least one flux sensing winding 242, and flux (magnitude and/or phase angle) is measured on the flux sensing winding by flux sensor 268. In a preferred variation of the flux measuring embodiment of FIG. 5, flux sensing windings are present near both teeth. Resulting signals can be processed by a computer 270 which is adapted to use the signals to detect core faults.

In the embodiment of FIG. 6, magnetic yoke 750 is adapted for being positioned near two non-adjacent teeth 22. In this embodiment, it is expected that magnetic flux can travel more deeply into the back iron 11 portion of core 12 than in the embodiment of FIG. 5.

Additionally, FIG. 6 illustrates an embodiment wherein the magnetic yoke further includes a shorting element 772 contacting at least one tooth between the two non-adjacent teeth and shorting laminations of the at least one tooth. Short-circuiting the laminations during testing is useful because the dependence on stator keybars (not shown) to provide a positive short circuit is then rendered irrelevant. Thus, the chance of a fault remaining undetected is substantially reduced. Shorting element 772 comprises an electrically conductive and compliant material such as copper-wool or indium, for example. Shorting element 772 is preferably attached to the magnetic yoke, and, in one embodiment is attached by a guide element 773 which is attached to a guide support 774. If the guide element comprises a spring or other flexible element, for example, then the shorting element can be gently pushed against the tooth without damaging the tooth laminations.

Applying leads 775 and 777 to shorting element 772, as shown in FIG. 6, permits the transmission of voltage or current from the shorting element which can serve as an alternative or additional signal to the signals described with respect to FIG. 5. The strength of the signal from leads 775 and 777 is expected to be proportional to the distance of the fault (short circuit) from the magnetic yoke. In a preferred embodiment, the leads are attached at opposing axial surfaces of the shorting element.

In FIG. 7, the magnetic yoke comprises a laminated bar 552 spanning a plurality of teeth and preferably having rectangular laminations which are again parallel to laminations of the teeth.

The embodiment of FIG. 8 is a variation wherein the magnetic yoke is adapted for being positioned at any of a number of angles. More specifically, in FIG. 8, magnetic yoke 662 comprises two arms 653 and 655 coupled by a hinge 657. In an alternative embodiment, yokes without hinges can be fabricated with predetermined angles.

In the embodiments of FIGS. 9–12, the magnetic yokes 350, 450, 850, and 950 are positioned near one tooth having air gap surfaces 23 (between the core and the shaft), side surfaces 25 (between adjacent teeth), and end surfaces 27 (on exposed or outer ends of the core).

Figure 9:
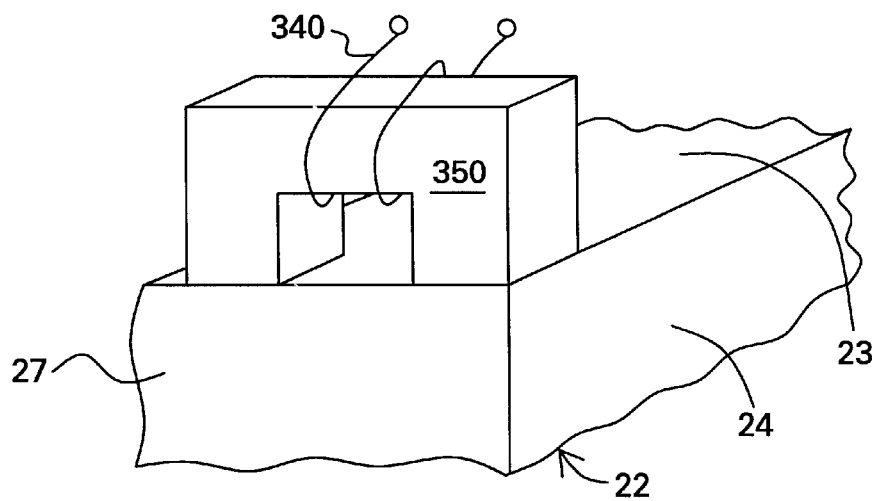

In the embodiment of FIG. 9, magnetic yoke 350 is positioned on air gap surface 23 of tooth 22. This embodiment is particularly useful for testing for faults in the tooth that are close to the air gap surface.

Figure 10:
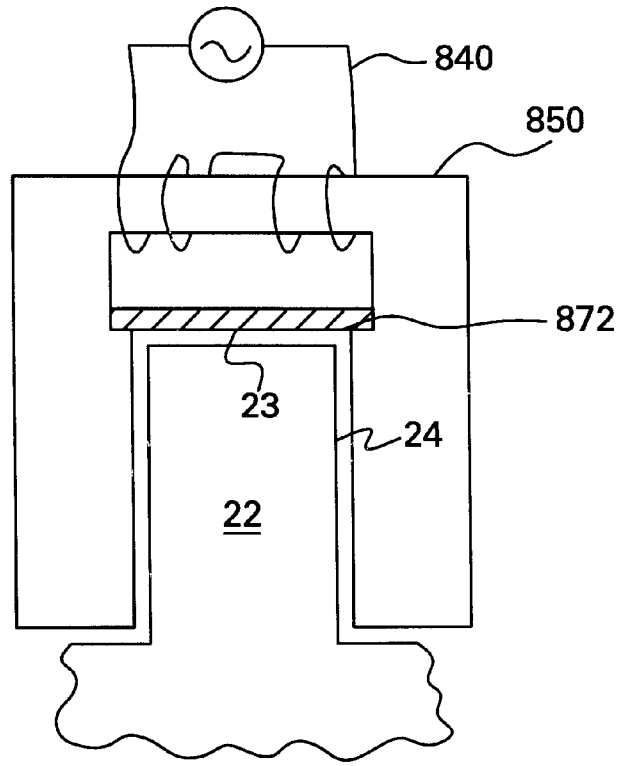
Figure 11:
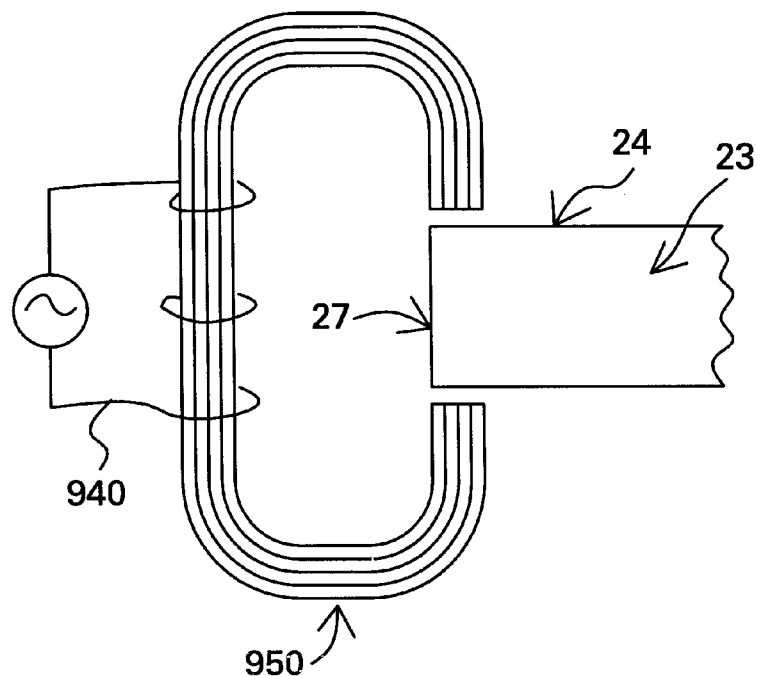
Figure 12:
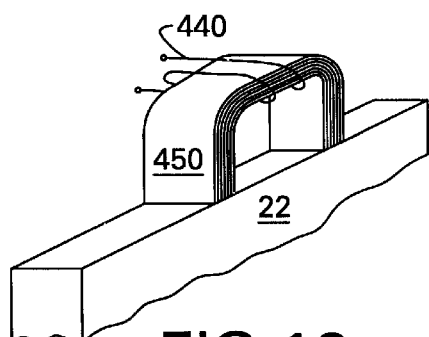

In the embodiment of FIGS. 10–11, magnetic yoke 850 or 950 is adapted for being positioned around tooth 22. More specifically, in the embodiment of FIG. 10, a U-shaped yoke 850 is positioned around a portion of the air gap and side surfaces. Again is it recommended that a series of axial movements and measurements be made. In a similar manner as discussed with respect to FIG. 6, a shorting element 872 can optionally be used to further focus the current induced by a fault. In the example of FIG. 10, the short is held directly on the yoke with an adhesive (not shown) for example. Alternatively, a guide element, such as discussed with respect to FIG. 6, can be used. If the short is designed to have flexibility in positioning, a number of different tooth heights and/or widths can be tested with a common magnetic yoke. It is expected that the FIG. 10 embodiment will be particularly useful for testing a more significant portion of the tooth than the FIG. 9 embodiment.

FIG. 11 illustrates an embodiment that is useful for testing portions of a tooth 22 that are near an end surface 27. In some embodiments, a core is stepped such that the length of material in the stator core decreases step-wise towards the ends of the core. Thus a yoke of the type in FIG. 10 that covers most of the side surfaces in the middle of the core might be longer than desired for measuring tooth flux towards an end of the core. In such embodiments, either a separate, shorter magnetic yoke of the type shown in FIG. 10 can be used, or a magnetic yoke 950 of the type shown in FIG. 11 may be used. As in all the embodiments of the present invention, it is preferred that the direction of lamination of the yoke be the same as the direction of lamination of the core. Thus the direction of lamination of yoke 950 in FIG. 11 is preferably shifted ninety degrees from that of yoke 850 in FIG. 10.

Regardless of which of the one or more magnetic yoke embodiments of FIGS. 5–12 are selected, the steps of supplying current, measuring the resulting signal, and using the measured signal to detect core faults are typically repeated such that a plurality of signals are used to detect core faults. The measurements can be performed, for example, by axially moving the magnetic yoke relative to the at least one tooth. Preferably, measurements are made until all regions of the core have been tested.

Additionally, the type of measurement can vary at individual positions or with the axial movement. For example, arbitrary waveform excitation can be applied. An "arbitrary waveform" may have any shape, amplitude, or frequency and may include pulses, sine waves, square waves, triangular waves, or chirp waves (frequency modulated waves), for example. Several specific embodiments are discussed below for purposes of example.

In one embodiment, the magnitude of the supplied current is varied. Because the current required to provide magnetic flux into a small region of the core is low (about 5 amps, for example), excitation magnitude can be conveniently varied to obtain a range of surface flux densities. A response curve of magnitude and phase as the current (and thus the flux density) is varied can be used as a "signature" for the condition of the core.

In another embodiment, the frequency of the supply current is varied. Such variation is also possible due to the low excitation power requirements. Signal response as a function of frequency is helpful for identifying fault locations because the depth of flux penetration varies depending on the frequency of the current. Thus a resulting "signature" can provide an indication of the distance of a fault from the surface.

In both the current magnitude and current frequency variation embodiments, steady state is quickly reached. Thus, high excitations (full flux, for example) can be applied for a short time without overheating the core. Typically the same set of such variations is applied to each position of the core that is tested.

In another embodiment, pulses of current are supplied to the winding with one or more pulses being supplied at each position of the core that is tested. This embodiment is particularly useful if sharply cut off pulses (such as pulses that have fall times of less than or equal to about one millisecond, for example) are applied and the time rates of decay of the signals are measured. Using multiple pulses at each position may improve resolution.

Varying the supply current for different measurements and/or applying pulsed current can be used to improve fault detection accuracy and to improve specificity in fault location and severity. Furthermore, in most embodiments of the present invention, the rotor does not necessarily need to be removed to accomplish the measurements.

When arbitrary waveforms are used, various mechanical resonances of local regions are likely to be excited in the presence of a fault. For example, loose laminations will rattle or otherwise result in vibrations that are different from vibrations of tightly held laminations. In these embodiments, a core vibration sensor 269 can be used in addition to or instead of the aforementioned voltage and flux sensors. Examples of vibration sensors include air vibration sensors such as ears or microphones and mechanical vibration sensors such as accelerometers.

Figure 13:
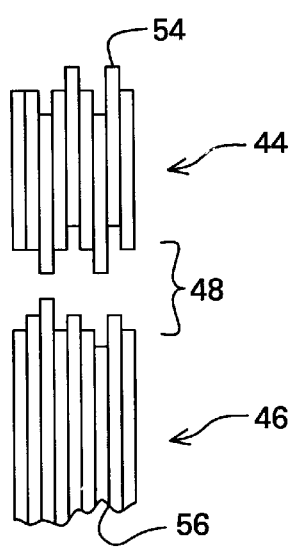
FIG. 13 is a sectional view of two sets of laminations having slightly uneven surfaces.
Figure 14:
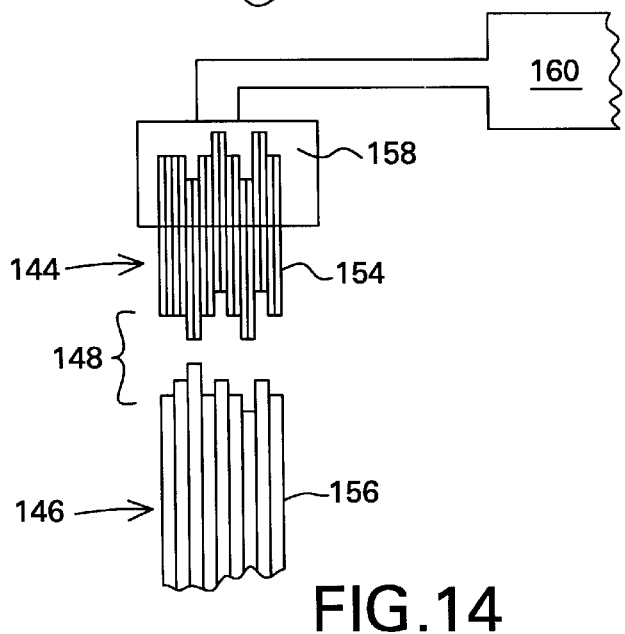
FIGS. 14 and 15 are sequential sectional views of one embodiment of the present invention wherein a compliant plunger temporarily improves contact between the laminations.
Figure 15:
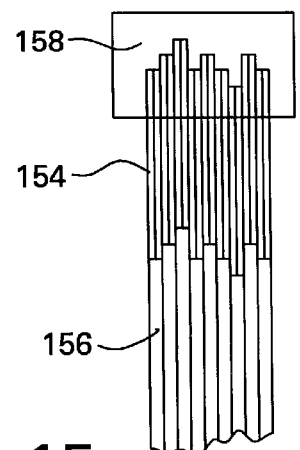

FIG. 13 is a sectional view of two sets of laminations having slightly uneven surfaces, and FIGS. 14 and 15 are sequential sectional views of one embodiment of the present invention wherein a compliant plunger temporarily improves contact between the laminations by minimizing the gaps between laminations.

In the embodiment illustrated in FIG. 5, magnetic yoke 250 comprises a laminated (laminations 210) U-shaped yoke, teeth 22 comprise laminated teeth of a laminated core, and the magnetic yoke and core have the same direction of lamination. In a more specific embodiment, the yoke comprises unbonded (that is, free to move) laminations about 14 mils (356 microns) thick and has a total thickness and height of about 1 inch (2.54 centimeters) by 1 inch (2.54 centimeters). In embodiments such as the example of FIG. 5 wherein it would be desirable to move a laminated first stack of laminations (144 in FIGS. 14 and 15/1250 in FIG.

5) along or as close as possible (due to increased gaps resulting in decreased sensitivity) along a second stack of laminations (146 in FIGS. 14 and 15/22 in FIG. 5), if both stacks of laminations do not have smooth surfaces, the laminations can be bent and result in damaging short circuits. Conventional techniques for smoothing include techniques such as machining, polishing, using sandpaper, for example. Without smoothing, typical roughness (distances between shortest and longest laminations) is on the order of about 10 mils (254 microns).

In one embodiment of the present invention, to prevent damage from sliding, the axial movement/positioning comprises lifting, axially moving, and lowering the magnetic yoke. In a more specific embodiment, a method for using a laminated magnetic yoke (250, 350, 450, or 552 in FIGS. 5–12 respectively) to measure a plurality of sections of a magnetic core (22 in FIG. 5, and 146 in FIG. 14) comprises: (a) providing a compliant plunger (158 in FIG. 14) for supporting yoke laminations (154 in FIG. 14) of the laminated magnetic yoke; (b) positioning the magnetic yoke near a section of the core; (c) lowering the magnetic yoke until at least some of the yoke laminations are in contact with core laminations (156 in FIG. 14) of the magnetic core; (d) taking a measurement; (e) lifting the magnetic yoke at least until none of the yoke laminations is in contact with any of the core laminations; (f) repeating (b)–(e) near at least one different section of the core. "Different" may comprise totally different or partially different (that is, overlapping) positions. Using partially overlapping positions minimizes "end effects" (that is, reduced signal strengths at the edges of the yoke) on the measured signals.

In a preferred embodiment, laminations 154 are thinner than laminations 156. In one example, the thickness of a lamination 154 is about 20% to about 80% the thickness of a lamination 156. Having thinner laminations 154 is useful because directly lining up same thickness type laminations can be difficult. Additionally, thinner laminations are more flexible, less likely to bend thicker laminations, and less likely to create short circuits.

The plunger may comprise a resilient material such as natural or synthetic rubber, for example. Controller 160 (which may comprise one or more integrated or separate sub-elements) can be used to accomplish the positioning and measuring. In one embodiment, controller 160 causes the plunger to be lowered a set distance. In another embodiment, the controller causes the plunger to be lowered until a predetermined level of mechanical resistance is detected.

For embodiments such as shown in FIG. 10, wherein yoke laminations are present on two side surfaces 24 of the core laminations, the repetitions of "position", "lower", and "lift" can be simultaneously performed on both side surfaces with "lower" meaning bring closer together and "lift" meaning move further away.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A method for detecting core faults comprising:
   (a) positioning a magnetic yoke near two non-adjacent teeth of the core, the magnetic yoke being wound by a winding;
   (b) supplying current to the winding to inject magnetic flux into the two non-adjacent teeth;
   (c) measuring a signal resulting from the injected magnetic flux; and
   (d) using the measured signal to detect core faults.
2. The method of claim 1 wherein (a) comprises positioning the magnetic yoke near two teeth.
3. The method of claim 2 wherein (a) comprises positioning the magnetic yoke near two adjacent teeth.
4. A method for detecting core faults comprising:
   (a) positioning a magnetic yoke near exactly one tooth of the core, the magnetic yoke being wound by a winding;
   (b) supplying current to the winding to inject magnetic flux into the tooth;
   (c) measuring a signal resulting from the injected magnetic flux; and
   (d) using the measured signal to detect core faults.
5. The method of claim 4 wherein (a) comprises positioning the magnetic yoke around the tooth.
6. The method of claim 5 wherein the magnetic yoke further includes a shorting element contacting and shorting laminations of the tooth.
7. The method of claim 6 wherein the magnetic yoke further includes a shorting element contacting at least one tooth between the two non-adjacent teeth and shorting laminations of the at least one tooth.
8. The method of claim 1 further comprising repeating (a)-(c) and using the plurality of resulting measured signals to detect core faults in (d).
9. The method of claim 1 wherein (a) comprises positioning the magnetic yoke near one tooth.
10. The method of claim 9 wherein (a) comprises positioning the magnetic yoke around the one tooth.
11. A method for detecting core faults comprising:
    (a) positioning a magnetic yoke near at least one tooth of the core, the magnetic yoke being wound by a winding;
    (b) supplying current having an arbitrary waveform to the winding to inject magnetic flux into the at least one tooth of the core;
    (c) measuring a plurality of signals resulting from the injected magnetic flux; and
    (d) using the plurality of resulting measured signals to detect core faults.
12. The method of claim 11 further including detecting voltage or current from the shorting element.
13. The method of claim 1 further comprising repeating (a)–(c) and using the plurality of resulting measured signals to detect core faults in (d).
14. The method of claim 13 wherein, when repeating (a)–(c), positioning comprises axially moving the magnetic yoke relative to the at least one tooth.
15. A method for detecting core faults comprising:
    (a) repeating, at different positions of the core,
       (1) positioning a magnetic yoke near two teeth of the core, the magnetic yoke being wound by a winding;
       (2) supplying current of varying frequency to the winding in inject magnetic flux into the two teeth of the core; and
       (3) measuring a plurality of signals resulting from the injected magnetic flux; and
    (b) using the plurality of resulting measured signals to detect core faults.
16. A method for detecting core faults comprising:
    (a) repeating, at different positions of the core,
       (1) positioning a magnetic yoke near two teeth of the core, the magnetic yoke being wound by a winding;
       (2) supplying current of varying magnitude to the winding to inject magnetic flux into the two teeth of the core;

(3) measuring a plurality of signals resulting from the injected magnetic flux; and (b) using the plurality of resulting measured signals to detect core faults.

17. The system of claim 16 wherein the at least one magnetic yoke comprises a bar-shaped yoke.

18. A system for detecting core faults comprising:
(a) at least one magnetic yoke wound by a winding and adapted for being positioned near two non-adjacent teeth of the core;
(b) a current supply for supplying current to the winding to inject magnetic flux into the two non-adjacent teeth of the core;
(c) a sensor for measuring a signal resulting from the injected magnetic flux; and
(d) a computer for using the measured signal to detect core faults.

19. The method of claim 18 wherein (b) comprises supplying sharply cut off pulses, and (c) comprises measuring the time rate of decay of the resulting measured signals.

20. A method for detecting core faults comprising: (a) repeating, at different positions of the core, (1) positioning a magnetic yoke near two teeth of the core, the magnetic yoke being wound by a winding; (2) supplying current to the winding to inject magnetic flux into the two teeth of the core; and (3) measuring a signal resulting from the injected magnetic flux; and (b) using the measured signals to detect core faults.

21. The system of claim 18 wherein the at least one magnetic yoke is adapted for being positioned at any of a number of angles.

22. A system for detecting core faults comprising: (a) at least one magnetic yoke wound by a winding for being positioned near at least one tooth of the core; (b) a current supply for supplying current to the winding to inject magnetic flux into the at least one tooth of the core; (c) a sensor for measuring a signal resulting from the injected magnetic flux; and (d) a computer for using the measured signal to detect core faults.

23. A system for detecting core faults comprising:
(a) at least one magnetic yoke wound by a winding and adapted for being positioned near exactly one tooth;
(b) a current supply for supplying current to the winding to inject magnetic flux into the tooth;
(c) a sensor for measuring a signal resulting from the injected magnetic flux; and
(d) a computer for using the measured signal to detect core faults.

24. The system of claim 23 wherein the at least one magnetic yoke is adapted for being positioned around the tooth.

25. The system of claim 24 wherien the magnetic yoke further includes a shorting element contacting and shorting laminations of the tooth.

26. A system for detecting core faults comprising:
(a) at least one magnetic yoke wound by a winding for being positioned near at least one tooth of the core;
(b) a current supply adapted to supply a current having an arbitrary waveform to the winding to inject magnetic flux into the at least one tooth of the core;
(c) a sensor for measuring a signal resulting from the injected magnetic flux; and
(d) a computer for using the measured signal to detect core faults.

27. The system of claim 22 the at least one magnetic yoke is adapted for being positioned near two adjacent teeth.

28. The system of claim 22 wherein the at least one magnetic yoke is adapted for being positioned near two non-adjacent teeth.

29. The system of claim 28 wherein the at least one magnetic yoke further includes a shorting element contacting at least one tooth between the two non-adjacent teeth and shorting laminations of the at least one tooth.

30. The system of claim 29 further including leads for transmitting voltage or current from the shorting element.

31. The system of claim 27 wherein the at least one magnetic yoke is adapted for being positioned at any of a number of angles.

32. A method for stacking a core comprising:
(a) forming a stack of a plurality of core laminations;
(b) positioning a magnetic yoe near at least one tooth of the stack, the magnetic yoke being wound by a winding;
(c) supplying current to the winding to inject magnetic flux into the at least one tooth;
(d) measuring a signal resulting from the injected magnetic flux;
(e) using the measured signal to detect core faults;
(f) if no core faults are detected in the stack, using the stack as part of the core, and if core faults are detected, not using the stack as port of the core; and
(g) forming an additional stack of a plurality of core laminations and repeating (b)-(f) for the additional stack.

33. The system of claim 26 wherein the sensor comprises a vibration sensor.

* * * * *

UNITED STATES PATENT AND TRADEMARK OFFICE
CERTIFICATE OF CORRECTION

PATENT NO. : 6,469,504 B1
APPLICATION NO. : 09/575715
DATED : October 22, 2002
INVENTOR(S) : Gerald Burt Kliman et al.

It is certified that error appears in the above-identified patent and that said Letters Patent is hereby corrected as shown below:

IN THE CLAIMS:

Claims 2, 3, 7, 9-10, 12-15, 17, 19, 20, 22, 25, and 27-32 should be rewritten as follows:

25. The system of claim 24 wherein the magnetic yoke further includes a shorting element contacting and shorting laminations of the tooth.

27. A method for using a laminated magnetic yoke to test a plurality of sections of a magnetic core comprising:
(a) providing a compliant plunger for supporting yoke laminations of the laminated magnetic yoke;
(b) positioning the magnetic yoke near a section of the core;
(c) lowering the magnetic yoke until at least some of the yoke laminations are in contact with core laminations of the magnetic core;
(d) taking a measurement;
(e) lifting the magnetic yoke at least until none of the yoke laminations is in contact with any of the core laminations;
(f) repeating (b)-(e) near at least one different section of the core.

28. The method of claim 27 wherein (a) comprises providing a compliant plunger supporting yoke laminations that are thinner than the core laminations.

29. An apparatus comprising:
(a) a compliant plunger; and
(b) a magnetic yoke comprising a plurality of yoke laminations supported by the compliant plunger.

30. A system for using a laminated magnetic yoke to test at least one section of a magnetic core comprising:
(a) a compliant plunger for supporting yoke laminations of the laminated magnetic yoke; and
(b) a controller for
(1) positioning the magnetic yoke near a section of the core and lowering the magnetic yoke until at least some of the yoke laminations are in contact with core laminations of the magnetic core,
(2) taking a measurement, and
(3) lifting the magnetic yoke at least until none of the yoke laminations is in contact with any of the core laminations.

UNITED STATES PATENT AND TRADEMARK OFFICE
CERTIFICATE OF CORRECTION

PATENT NO. : 6,469,504 B1
APPLICATION NO. : 09/575715
DATED : October 22, 2002
INVENTOR(S) : Gerald Burt Kliman et al.

It is certified that error appears in the above-identified patent and that said Letters Patent is hereby corrected as shown below:

IN THE CLAIMS:

Claims 2, 3, 7, 9-10, 12-15, 17, 19, 20, 22, 25, and 27-32 appear incorrectly and should be rewritten as follows:

31. The system of claim 30 wherein the yoke laminations are thinner than the core laminations.

32. A method for stacking a core comprising:
(a) forming a stack of a plurality of core laminations;
(b) positioning a magnetic yoke near at least one tooth of the stack, the magnetic yoke being wound by a winding;
(c) supplying current to the winding to inject magnetic flux into the at least one tooth;
(d) measuring a signal resulting from the injected magnetic flux;
(e) using the measured signal to detect core faults;
(f) if no core faults are detected in the stack, using the stack as part of the core, and if core faults are detected, not using the stack as part of the core; and
(g) forming an additional stack of a plurality of core laminations and repeating (b)-(f) for the additional stack.

Signed and Sealed this

Twenty-fourth Day of June, 2008

JON W. DUDAS
*Director of the United States Patent and Trademark Office*